(12) United States Patent
Nishida et al.

(10) Patent No.: US 7,053,079 B2
(45) Date of Patent: May 30, 2006

(54) DIHYDROXY (3-PYRIDYL) BORANE COMPOUNDS

(75) Inventors: Mayumi Nishida, Chiba (JP); Tsuyoshi Tagata, Sodegaura (JP); Masaki Shimada, Ichihara (JP)

(73) Assignee: KOEI Chemical Company, Limited, Osaka (JP)

( * ) Notice: Subject to any disclaimer, the term of this patent is extended or adjusted under 35 U.S.C. 154(b) by 0 days.

(21) Appl. No.: 10/493,847

(22) PCT Filed: Nov. 27, 2002

(86) PCT No.: PCT/JP02/12357

§ 371 (c)(1),
(2), (4) Date: Apr. 27, 2004

(87) PCT Pub. No.: WO03/045958

PCT Pub. Date: Jun. 5, 2003

(65) Prior Publication Data

US 2004/0254076 A1 Dec. 16, 2004

(30) Foreign Application Priority Data

Nov. 28, 2001 (JP) ............................ 2001-363381

(51) Int. Cl.
*C07F 5/02* (2006.01)
*A61K 31/44* (2006.01)

(52) U.S. Cl. .................. 514/188; 514/277; 546/13

(58) Field of Classification Search ................ 546/13; 514/188, 277
See application file for complete search history.

(56) References Cited

U.S. PATENT DOCUMENTS 5,358,948 A 10/1994 Bradshaw et al.
6,228,810 B1 5/2001 Rohl et al.

FOREIGN PATENT DOCUMENTS

| DE | 42 18 978 A1 | 12/1993 |
|---|---|---|
| DE | 4218978 A1 | 12/1993 |
| EP | 0690061 A1 * | 1/1996 |
| WO | WO 91/04249 A1 * | 9/1990 |
| WO | WO 93/06084 A1 | 4/1993 |
| WO | WO 95/28400 A1 * | 10/1995 |
| WO | WO 98/12179 A1 | 3/1998 |

OTHER PUBLICATIONS

Bromidge et al, J. Med. Chem, vol. 43, pp. 1123-1134, 2000.*
Lehmann et al, Chem. Eur. J, vol. 5, No. 3, pp. 854-859, 1999.*
Achab et al, Tetrahedron Letters, vol. 34, No. 13, pp. 2127-2130, 1993.*
Lehmann Uwe et al., *Chem. Eur. J.*, vol. 5, No. 3, (1999), pp. 854-859.
Lehmann, Uwe et al., 5,5''-Disubstituted 2,2':6',2''-terpyridines through and for metal-mediated cross-coupling chemistry, A European Journal, 1999, vol. 5, No. 3, pp. 854 to 859.

* cited by examiner

*Primary Examiner*—Zinna N. Davis
(74) *Attorney, Agent, or Firm*—Birch, Stewart, Kolasch & Birch, LLP

(57) ABSTRACT

A dihydroxy(3-pyridyl)borane compound of the formula (1):

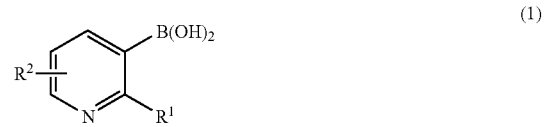

(1)

wherein $R^1$ represents a hydrogen atom, halogen atom or alkoxycarbonylamino group; $R^2$ represents a hydrogen atom, halogen atom, alkyl group or fluoroalkyl group; with the proviso that the case wherein both $R^1$ and $R^2$ are hydrogen atoms is excepted.

6 Claims, No Drawings

DIHYDROXY (3-PYRIDYL) BORANE COMPOUNDS

TECHNICAL FIELD

The present invention relates to novel dihydroxy(3-pyridyl)borane compounds and a production method thereof.

BACKGROUND ART

It is described in JP 54-144379A that pyridine compounds having an aromatic hydrocarbyl group or aromatic heterocyclic group at 3-position are important intermediates for producing medicaments, plant protectants and so on, and that it is desired to develop a beneficial production method thereof. Further, it is known that some 3-substituted pyridines are useful for perfume in JP 57-16862A, JP 4-230665A and so on.

DISCLOSURE OF INVENTION

The present invention provides novel dihydroxy(3-pyridyl)borane compounds of the formula (1) below:

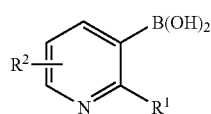
(1)

wherein $R^1$ represents a hydrogen atom, halogen atom or alkoxycarbonylamino group; $R^2$ represents a hydrogen atom, halogen atom, alkyl group or fluoroalkyl group; the carbon number of the alkoxy in said alkoxycarbonylamino group is 1 to 4, and each of the carbon number of said alkyl group and said fluoroalkyl group is 1 to 4; with the proviso that the case wherein both $R^1$ and $R^2$ are hydrogen atoms is excepted;

which are raw materials for producing 3-substituted pyridine compounds.

The present invention also provides a method for producing the dihydroxy(3-pyridyl)borane compounds of the formula (1).

In the dihydroxy(3-pyridyl)borane compounds of the present invention, examples of the halogen atom for $R^1$ in the formula (1) include fluorine, chlorine, bromine and iodine. Examples of the alkoxycarbonylamino group are alkoxycarbonylamino group having C1–C4 straight or branched chain alkoxy group such as methoxycarbonylamino, ethoxycarbonylamino, propoxycarbonylamino, isopropoxycarbonylamino, butoxycarbonylamino and t-butoxycarbonylamino group.

Further, examples of the halogen atom for $R^2$ in the formula (1) include fluorine, chlorine, bromine and iodine; examples of the alkyl group are C1–C4 straight or branched chain lower alkyl group such as methyl, ethyl, propyl, isopropyl, butyl and t-butyl group; and examples of the fluoroalkyl group are C1–C4 alkyl group substituted by one or more fluorine atoms for hydrogen atoms such as monofluoromethyl, difluoromethyl, trifluoromethyl, 1-fluoroethyl, 1,2-difluoroethyl, 1,1,2-trifluoroethyl, 1,1,1,2-tetrafluoroethyl, 1,1,2,2-tetrafluoroethyl and 1,1,1,2,2-pentafluoroethyl group.

The dihydroxy(3-pyridyl)borane compounds of the present invention can be produced by the following method.

The dihydroxy(3-pyridyl)borane compounds of the formula (1) wherein $R^1$ represents a halogen atom or alkoxycarbonylamino group, namely the dihydroxy(2-halogeno-3-pyridyl)borane compounds and the dihydroxy(2-alkoxycarbonylamino-3-pyridyl)borane compounds of the formula (4):

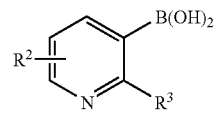
(4)

wherein $R^2$ represents a hydrogen atom, halogen atom, alkyl group or fluoroalkyl group; $R^3$ represents a halogen atom or alkoxycarbonylamino group; the carbon number of said alkyl group and fluoroalkyl group is 1 to 4; and the carbon number of the alkoxy in said alkoxycarbonylamino group is 1 to 4;

can be easily produced by reacting a pyridine compound of the formula (2):

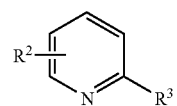
(2)

wherein $R^2$ and $R^3$ represent the same meanings mentioned above, with lithium amide in an organic solvent, and conducting a reaction by adding a trialkoxyborane compound of the formula (3):

(3)

wherein $R^4$ represents a C1–C4 alkyl group, to the reaction mixture, and then reacting the resulted reaction mixture with water.

The organic solvent is not restricted as long as it is inactive in the reaction. Examples of the organic solvent include ethers such as 1,2-dimethoxyethane, diethyl ether and tetrahydrofuran; aliphatic hydrocarbons such as hexane, heptane and octane; and mixtures thereof.

Typical examples of the pyridine compound of the formula (2) include 2-chloropyridine, 2-bromopyridine, 2,5-dichloropyridine, 2-chloro-6-methylpyridine, 2-chloro-5-trifluoromethylpyridine and 2-t-butoxycarbonylaminopyridine.

Typical examples of the lithium amide include lithium dialkylamide such as lithium diethylamide and lithium diisopropylamide; lithium polymethyleneimide such as lithium pyrrolidide and lithium piperidide; and lithium 2,2',6,6'-tetramethylpiperidide. Among them, lithium di(C1–C4 alkyl)amide is preferably used. Said lithium amide is usually prepared from a secondary amine and an alkyllithium. Examples of the secondary amine include dialkylamine such as diethylamine, diisopropylamine; polymethyleneimine such as pyrrolidine and piperidine; and 2,2',6,6'-tetramethylpiperidine. Examples of the alkyllithium include C1–C4 alkyllithium such as methyllithium and butyllithium; phenyllithium; and naphthyllithium. The lithium amide is preferably prepared from the secondary amine and the alkyllithium just before the reaction. For example, it can be easily prepared almost quantitatively by mixing equimolar secondary amine and alkyllithium under stirring in an organic solvent. The pyridine compound of the formula (2) is added to the prepared lithium amide solution and mixed under stirring, and the reaction mixture is allowed to react with trialkoxyborane compound of the formula (3), and subsequently water to give the dihydroxy(2-halogeno-3-pyridyl)borane compound or dihydroxy(2-alkoxycarbonylamino-3-pyridyl)borane compound of the formula (4). In the preparation of lithium amide, the reaction temperature of the secondary amine with the alkyllithium is preferably −80 to 0° C.

The reaction temperature of the pyridine compound of the formula (2) with the lithium amide is preferably −80 to −20° C. The amount of the lithium amide used in the reaction is usually between 1.0 and 3.5 moles per 1 mole of the pyridine compound of the formula (2), and the amount of the organic solvent is usually between 1 and 100 parts by weight per 1 part by weight of the pyridine compound of the formula (2).

In the trialkoxyborane compound of the formula (3), examples of the alkyl group given by $R^4$ in the formula (3) include C1–C3 straight or branched chain alkyl group, namely, methyl, ethyl, propyl and isopropyl group, and typical examples of the trialkylborane compound include trimethoxyborane, triethoxyborane, tripropoxyborane and triisopropoxyborane. The amount of the trialkoxyborane compound of the formula (3) used in the reaction is usually between 1.0 and 3.5 moles per 1 mole of the pyridine compound of the formula (2). The reaction temperature of the trialkoxyborane compound of the formula (3) is preferably −80 to −20° C. as well as the reaction temperature of the pyridine compound of the formula (2) with the lithium amide.

The last reaction with water can be performed by only adding water to the reaction mixture and stirring well. The amount of the water used above is usually between 1 and 10 parts by weight per 1 part by weight of the pyridine compound of the formula (2). The reaction temperature is usually −80 to 50° C., preferably −30 to 30° C.

In the production method, it is thought that a 3-pyridyllithium compound of the formula (8):

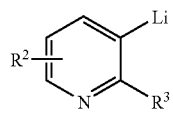

(8)

wherein $R^2$ and $R^3$ represent the same meanings mentioned above, is produced by the reaction of the pyridine compound of the formula (2) with the lithium amide. It is thought that said 3-pyridyllithium compound reacts with the trialkoxyborane compound of the formula (3) to give a dialkoxy(3-pyridyl)borane compound of the formula (9):

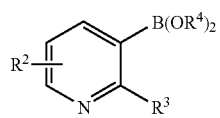

(9)

wherein $R^2$, $R^3$ and $R^4$ represent the same meanings mentioned above, and further that the obtained dialkoxy(3-pyridyl)borane compound is hydrolyzed to give the dihydroxy(2-halogeno-3-pyridyl)borane compound or dihydroxy(2-alkoxycarbonylamino-3-pyridyl)borane compound.

It is preferable to keep the reaction mixture being in anhydrous condition, because the alkyllithium, lithium amide and 3-pyridyllithium compound of the formula (8) tend to react with water to decompose easily. For example, it is preferable to use the organic solvent well dried for the reaction.

In the novel dihydroxy(3-pyridyl)borane compounds of the formula (1) wherein $R^1$ is a hydrogen atom, namely a compound of the formula (6):

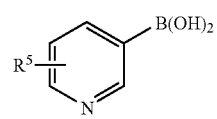

(6)

wherein $R^5$ represents a halogen atom, C1–C4 alkyl group or C1–C4 fluoroalkyl group;

can be easily produced by reacting a compound of the formula (5):

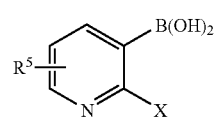

(5)

wherein X represents a halogen atom and $R^5$ represents the same meaning mentioned above, with hydrogen for dehalogenation in the presence of a hydrogenation catalyst and base in a solvent.

A catalyst having an efficacy reducing aromatic halides, such as noble metal catalyst including palladium catalyst and platinum catalyst, is used as the hydrogenation catalyst. In particular, preferable is a catalyst supported a noble metal such as palladium and platinum on a carrier such as silica gel, alumina, activated carbon, diatomaceous earth and calcium carbonate. In that case, the amount of the supported noble metal is usually 0.1–50 parts by weight, preferably 1–10 parts by weight per 100 parts by weight of the carrier. Further, the amount of the hydrogenation catalyst is usually 0.1–100 parts by weight, preferably 1–50 parts by weight per 100 parts by weight of the compound of the formula (5).

The bases used for the reaction are inorganic bases such as alkali hydroxide (e.g. potassium hydroxide, sodium hydroxide), alkaline earth hydroxide (e.g. barium hydroxide), alkaline earth oxide (e.g. magnesium oxide, calcium oxide), alkali acetate (e.g. sodium acetate, potassium acetate) and ammonia, and organic bases such as triethylamine. The amount of the base used in the reaction is usually between 1 and 20 moles, preferably between 1 and 5 moles per 1 mole of the compound of the formula (5).

As the solvent used for the reaction, water, alcohols and mixtures thereof are preferable. Among the alcohols, C1–C4 alcohol such as methanol, ethanol, propanol, isopropyl alcohol, butanol and sec-butyl alcohol is preferable. The amount of the solvent used for the reaction is usually between 1 and 100 parts by weight, preferably between 1 and 10 parts by weight per 1 part by weight of the compound of the formula (5). The reaction is carried out with or without pressure, usually at atmospheric pressure to 10 MPa, preferably at atmospheric pressure to 1.0 Mpa. The reaction temperature is usually 0 to 150° C., preferably 20 to 60° C.

The dihydroxy(3-pyridyl)borane compounds of the formula (1) can be isolated from the reaction mixture by conventional procedures such as filtration, neutralization, extract, concentration, distillation, recrystallization and/or column chromatography.

The dihydroxy(3-pyridyl)borane compound of the present invention readily changes to its anhydride under heating or the like. Namely, it readily changes to a boroxine compound of the formula (7):

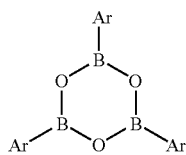
(7)

[wherein Ar represents a 3-pyridyl group of the formula:

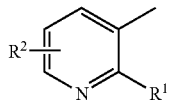

wherein $R^1$ and $R^2$ represent the same meanings mentioned above] by intermolecular dehydration-condensation. This boroxine compound can be easily derived to pyridine compounds having an aromatic hydrocarbyl group or aromatic heterocyclic group at 3-position as well as the dihydroxy(3-pyridyl)borane compound of the present invention.

Typical examples of the dihydroxy(3-pyridyl)borane compound of the formula (1) of the present invention include dihydroxy(2-chloro-3-pyridyl)borane, dihydroxy(2-bromo-3-pyridyl)borane, dihydroxy(2,5-dichloro-3-pyridyl)borane, dihydroxy(2-chloro-6-methyl-3-pyridyl)borane, dihydroxy(2-t-butoxycarbonylamino-3-pyridyl)borane and dihydroxy(2-chloro-5-trifluoromethyl-3-pyridyl)borane.

The dihydroxy(3-pyridyl)borane compound and its anhydride, boroxine compound, of the present invention are, for example, derived to intermediates of medicaments, plant protectants and so on, organic EL materials and liquid crystal materials by coupling reaction with an aromatic halide. The coupling reaction can be, for example, performed in the presence of palladium catalyst. It is usually carried out by using a base such as alkali carbonate and alkali hydroxide, triarylphosphine such as triphenylphosphine and palladium catalyst, in a solvent such as water and alcohol, under heating at approximately 50 to 150° C.

EXAMPLES

Hereinafter, the present invention is more concretely explained by examples, however, it should not be restricted by the examples below.

Example 1

A solution consisting of 2.11 ml (15 mmole) of diisopropylamine and 15 ml of anhydrous tetrahydrofuran was cooled to 0° C., and 9.8 ml of 1.53 mole/liter of n-butyllithium/hexane solution (15 mmole of n-butyllithium) were added dropwise thereto over 10 minutes and stirred to give a mixture containing lithium diisopropylamide. The obtained mixture was cooled to −78° C., and a solution consisting of 0.94 ml (10 mmole) of 2-chloropyridine and 10 ml of anhydrous tetrahydrofuran was added dropwise thereto over 20 minutes and stirred at the same temperature to allow to react for 2 hours. Further, a solution consisting of 1.14 ml (10 mmole) of trimethoxyborane and 10 ml of anhydrous tetrahydrofuran was added dropwise thereto over 20 minutes and stirred at the same temperature to allow to react for 2 hours. To the resulted reaction mixture, 2.4 ml of hydrous tetrahydrofuran (water content: approximately 16% by weight) were added dropwise at −78° C., and then allowed to stand to −10° C., and further 20 ml of water were added. The reaction mixture was allowed to stand at room temperature, to which 20 ml of ethyl acetate were added and mixed. The water layer was separated from the organic layer, adjusted to about 4.0 of pH with 10% by weight of hydrochloric acid and extracted with 30 ml of ethyl acetate twice. The ethyl acetate layers were combined, washed 20 ml of saturated brine, dried over anhydrous sodium sulfate and concentrated under reduced pressure. The obtained residue was purified by silica gel column chromatography [eluent, ethyl acetate:acetic acid=100:0.1] to give 1.04 g of reddish orange solid. The obtained solid is a mixture of dihydroxy (2-chloro-3-pyridyl)borane and a compound having a boroxine structure of the formula (4) which is its anhydride. The $^1$H-NMR of the mixture is as below. The yield was 66% calculated by converting to dihydroxy(2-chloro-3-pyridyl) borane.

$^1$H-NMR (D$_2$O, NaOD, MeOD; ppm) σ: 8.09–8.15 (m, 1H), 8.06, 8.04, 7.98 (each of these three peaks is dd, J=7.3 Hz, J=ca. 2.0 Hz, and the number of the proton is totally 1H), 7.28 (ddd, J=6.8 Hz, J=4.8 Hz, J=1.6 Hz, 1H)

Example 2

The same procedure as Example 1 except that 1.58 g (10 mmole) of 2-bromopyridine were used in place of 2-chloropyridine was performed to give 1.55 g of brown solid. The obtained solid is a mixture of dihydroxy(2-bromo-3-pyridyl) borane and a compound having a boroxine structure of the formula (4) which is its anhydride. The $^1$H-NMR of the mixture is as below. The yield was 77% calculated by converting to dihydroxy(2-bromo-3-pyridyl)borane.

$^1$H-NMR (D$_2$O, NaOD, MeOD; ppm) σ: 7.97–8.13 (m, 2H), 7.28–7.37 (m, 1H)

Example 3

The same procedure as Example 1 except that 1.28 g (10 mmole) of 2-chloro-6-methylpyridine were used in place of 2-chloropyridine and that 2.30 ml (10 mmole) of triisopropoxyborane were used in place of trimethoxyborane was performed to give 480 mg of yellow solid. The obtained solid is a mixture of dihydroxy(2-chloro-6-methyl-3-pyridyl)borane and a compound having a boroxine structure of the formula (4) which is its anhydride. The $^1$H-NMR of the mixture is as below. The yield was 28% calculated by converting to dihydroxy(2-chloro-6-methyl-3-pyridyl)borane.

¹H-NMR (D₂O, NaOD, MeOD; ppm) σ: 7.84–7.98 (m, 1H), 7.13 (dd, J=7.3 Hz, J=1.8 Hz, 1H), 2.40 (s, 3H)

Example 4

The same procedure as Example 1 except that 1.82 g (10 mmole) of 2-chloro-5-trifluoromethylpyridine were used in place of 2-chloropyridine was performed to give 572 mg of brown solid. The obtained solid is a mixture of dihydroxy (2-chloro-5-trifluoromethyl-3-pyridyl)borane and a compound having a boroxine structure of the formula (4) which is its anhydride. The ¹H-NMR of the mixture is as below. The yield was 25% calculated by converting to dihydroxy (2-chloro-5-trifluoromethyl-3-pyridyl)borane.

¹H-NMR (D₂O, NaOD, MeOD; ppm) σ: 8.45–8.51 (m, 1H), 8.39, 8.36, 8.29 (each of these three peaks is d, J=2.5 Hz, and the number of the proton is totally 1H)

Example 5

The same procedure as Example 1 except that 1.48 g (10 mmole) of 2,5-dichloropyridine were used in place of 2-chloropyridine was performed to give 770 mg of pale yellow solid. The obtained solid is a mixture of dihydroxy (2,5-dichloro-3-pyridyl)borane and a compound having a boroxine structure of the formula (4) which is its anhydride. The ¹H-NMR of the mixture is as below. The yield was 40% calculated by converting to dihydroxy(2,5-dichloro-3-pyridyl)borane.

¹H-NMR (D₂O, NaOD, MeOD; ppm) σ: 8.15 (s, 1H), 7.65, 7.62, 7.57 (each of these three peaks is s, and the number of the proton is totally 1H)

Example 6

The same procedure as Example 1 except that 1.94 g (10 mmole) of 2-butoxycarbonylaminopyridine were used in place of 2-chloropyridine was performed to give 47 mg of white solid. The obtained solid is a mixture of (2-butoxycarbonylamino-3-pyridyl)borane and a compound having a boroxine structure of the formula (4) which is its anhydride. The ¹H-NMR of the mixture is as below. The yield was 2.0% calculated by converting to dihydroxy(2-butoxycarbonylamino-3-pyridyl)borane.

¹H-NMR (D₂O, NaOD, MeOD; ppm) σ: 8.24 (m, 1H), 7.81 (m, 1H), 7.67 (d, J=8.4 Hz, 1H), 7.11 (ddd, J=6.5, J=5.3, J=0.8 Hz, 1H), 1.55 (s, 1H)

INDUSTRIAL APPLICABILITY

The dihydroxy(3-pyridyl)borane compounds of the present invention are useful intermediates for producing pyridine compounds, having an aromatic hydrocarbyl group or aromatic heterocyclic group at 3-position, which are important intermediates for producing medicaments, plant protectants and so on.

What is claimed is:

1. A dihydroxy(3-pyridyl)borane compound of the formula (1):

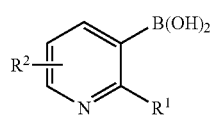

(1)

wherein R¹ represents a chlorine atom or alkoxycarbonylamino group; R² represents a hydrogen atom or alkyl group; the carbon number of the alkoxy in said alkoxycarbonylamino group being 1 to 4, and the carbon number of said alkyl group being 1 to 4;
or an anhydride thereof.

2. The dihydroxy(3-pyridyl)borane compound according to claim 1, wherein R¹ represents a chlorine atom; and R² represents a hydrogen atom or alkyl group; or an anhydride thereof.

3. The dihydroxy(3-pyridyl)borane compound according to claim 1, wherein R¹ represents an alkoxycarbonylamino group; and R² represents a hydrogen atom; or an anhydride thereof.

4. A method for producing a dihydroxy(3-pyridyl)borane compound, of the formula (1):

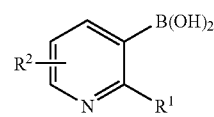

(1)

wherein R¹ represents a chlorine atom or alkoxycarbonylamino group; R² represents a hydrogen atom or alkyl group; the carbon number of the alkoxy in said alkoxycarbonylamino group being 1 to 4, and the carbon number of said alkyl group being 1 to 4; or an anhydride thereof, which comprises reacting a pyridine compound of the formula (2):

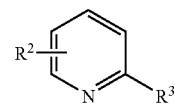

(2)

wherein R² represents a hydrogen atom or alkyl group; and R³ represents a chlorine atom or alkoxycarbonylamino group; the carbon number of the alkoxy in said alkoxycarbonylamino group being 1 to 4,
with a lithium amide in an organic solvent, reacting the reaction mixture with a trialkoxyborane compound of the formula (3):

B(OR⁴)₃   (3)

wherein R¹ represents an alkyl group,
and then reacting the resultant reaction mixture with water.

5. The method for producing a dihydroxy(3-pyridyl) borane compound of the formula (6):

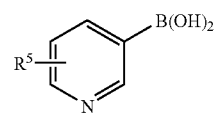

(6)

wherein R⁵ represents a halogen atom, alkyl group or fluoroalkyl group, each of the carbon number of said alkyl group is and said fluoroalkyl group being 1 to 4, or an anhydride thereof, which comprises reacting a dihydroxy(3-pyridyl)borane compound of the formula (5),

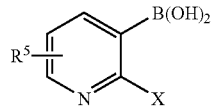
(5)

wherein X represents a halogen atom; and $R^5$ has the same meaning as recited above, with hydrogen in the presence of a hydrogenation catalyst and a base in a solvent.

6. The dihydroxy(3-pyridyl)borane compound according to claim 1, wherein $R^1$ represents an alkoxycarbonylamino group; R2 represents a hydrogen atom or alkyl group, the carbon number of the alkoxy in said alkoxycarbonylamino group is 1 to 4, and the carbon number of said alkyl group is 1 to 4; or an anhydride thereof.

* * * * *